(12) United States Patent
Wardle et al.

(10) Patent No.: US 6,488,030 B1
(45) Date of Patent: Dec. 3, 2002

(54) ARTICULATING GUIDE ARM FOR MEDICAL APPLICATIONS

(75) Inventors: John L. Wardle, San Clemente, CA (US); Mark A. Ritchart, Murrieta, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/496,518

(22) Filed: Feb. 2, 2000

Related U.S. Application Data

(63) Continuation of application No. 08/804,913, filed on Feb. 25, 1997.
(60) Provisional application No. 60/012,302, filed on Feb. 26, 1996.

(51) Int. Cl.$^7$ ................................................ A61G 15/00
(52) U.S. Cl. ........................................ 128/845; 248/278
(58) Field of Search ................................ 128/845, 846, 128/878, 879, 882; 602/32–40; 248/278

(56) References Cited

U.S. PATENT DOCUMENTS

| | | | | |
|---|---|---|---|---|
| 1,580,507 A | * | 4/1926 | Lidgett | 602/33 |
| 2,458,950 A | * | 1/1949 | Luzardo | 128/845 |
| 2,718,886 A | * | 9/1955 | Sutton | 602/33 |
| 4,143,652 A | * | 3/1979 | Meier | 128/20 |
| 4,307,475 A | | 12/1981 | Schmidt | 4/263 |
| 4,457,300 A | | 7/1984 | Budde | 128/20 |
| 4,573,452 A | | 3/1986 | Greenberg | 128/20 |
| 4,653,509 A | | 3/1987 | Oloff et al. | 128/749 |
| 4,836,133 A | | 6/1989 | Wohrle | 118/410 |

(List continued on next page.)

FOREIGN PATENT DOCUMENTS

| | | | |
|---|---|---|---|
| DE | 2311257 | 9/1974 | ........... A61B/19/00 |
| EP | 0654244 | 5/1995 | |
| EP | 0 654 244 B1 | 8/1999 | ............ A61B/8/00 |
| GB | 1496804 | 1/1978 | |
| GB | 1 496 804 | 1/1978 | ............ A61B/1/26 |
| WO | WO 94/06352 | 3/1994 | ............ A61B/6/04 |

*Primary Examiner*—Michael A. Brown

(57) ABSTRACT

A device is provided for stabilizing and positioning an otherwise hand-held medical instrument, such as a biopsy power driver and probe, to ensure the ability to accurately place the probe into the breast and maintain position relative to a particular tissue site from any desired entry point. The device comprises a main arm having a generally vertical portion and a generally horizontal portion. A clamping assembly permits attachment of the apparatus to a stationary object, which is preferably an examination table, and includes a locking clamp having a gripping mode and a releasing mode for alternately gripping and releasing the main arm, and a lever assembly for actuating the locking clamp between the gripping mode and the releasing mode. A horizontal clamp, attached to the generally horizontal portion of the main arm, provides support for an articulating arm assembly having a first arm portion, or upper arm, and a second arm portion, or forearm, wherein the upper arm and forearm are attached together by an elbow joint, so that they may be articulated relative to one another about a common axis disposed through the elbow. A mounting bracket for securing the biopsy power driver and probe is attached to a distal end of the forearm. The elbow joint attaching the upper arm and forearm of the articulating arm assembly comprises a spring loaded counterbalance mechanism which functions to support the weight of the medical instrument, thereby giving the instrument a weightless feel during the positioning process, which prevents fatigue on the part of a user and therefore permits more delicate and precise movements of the instrument.

10 Claims, 6 Drawing Sheets

U.S. PATENT DOCUMENTS

| | | | |
|---|---|---|---|
| 4,852,552 A | 8/1989 | Chaux | 128/20 |
| 4,863,133 A * | 9/1989 | Bonnell | 248/278 |
| 4,867,404 A | 9/1989 | Harrington et al. | 248/231.4 |
| 4,883,346 A | 11/1989 | Aoki et al. | 350/423 |
| 4,971,037 A | 11/1990 | Pelta | 128/20 |
| 4,993,862 A | 2/1991 | Pelta | 403/59 |
| 5,019,092 A | 5/1991 | Klintmalm | 606/207 |
| 5,056,535 A * | 10/1991 | Bonnell | 128/882 |
| 5,113,846 A | 5/1992 | Hiltebrandt et al. | 128/20 |
| 5,184,601 A | 2/1993 | Putman | 128/4 |
| 5,340,072 A | 8/1994 | Halbirt | 248/219 |
| 5,351,676 A | 10/1994 | Putman | 128/4 |
| 5,372,147 A | 12/1994 | Lathrop, Jr. et al. | 128/898 |
| 5,380,338 A | 1/1995 | Christian | 606/130 |
| 5,391,180 A | 2/1995 | Tovey et al. | 606/205 |
| 5,441,042 A | 8/1995 | Putman | 601/109 |
| 5,540,649 A * | 7/1996 | Bonnell | 600/114 |
| 5,616,117 A * | 4/1997 | Dinkler | 600/232 |
| 6,085,749 A | 7/2000 | Wardle et al. | 128/845 |

\* cited by examiner

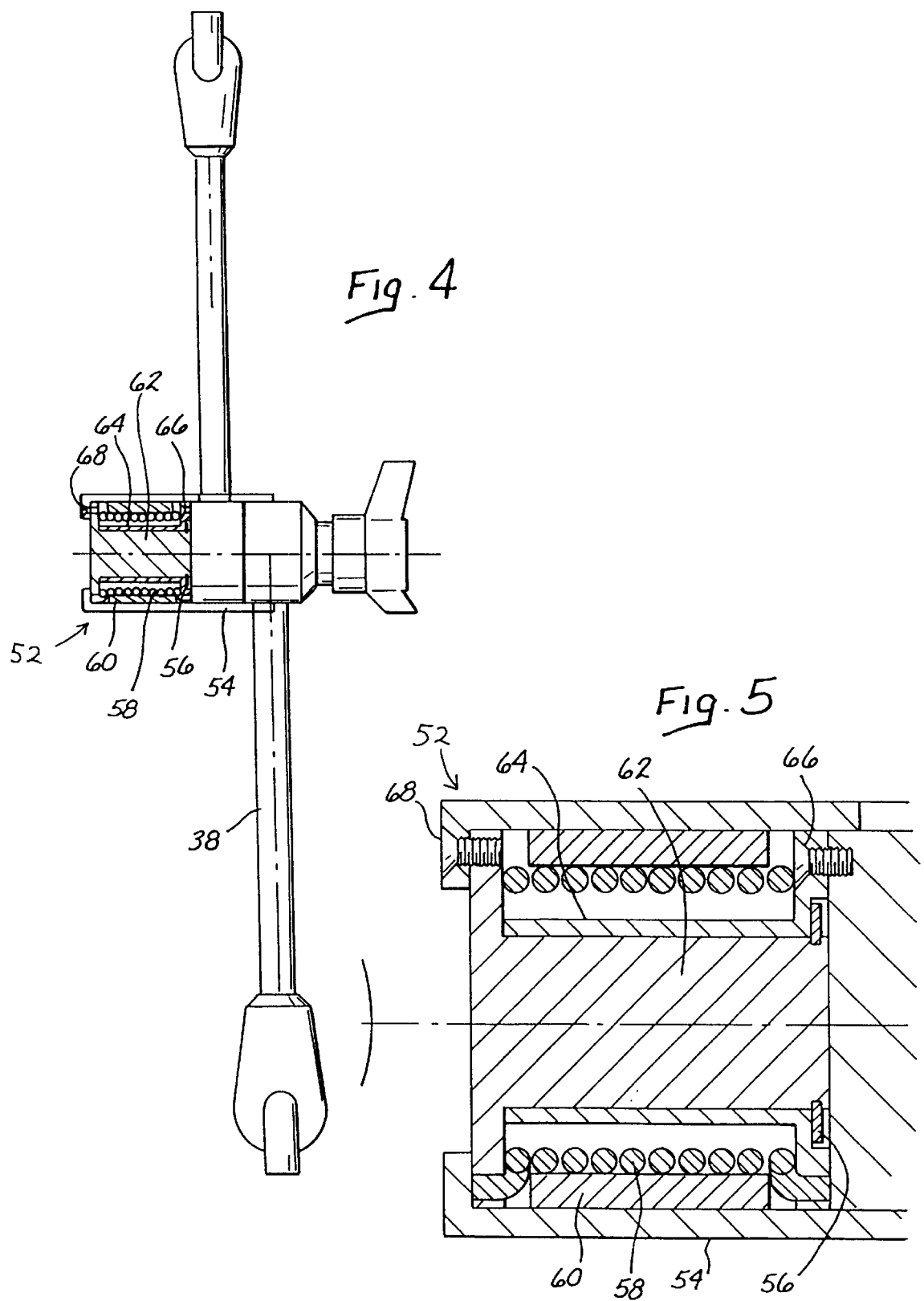

ARTICULATING GUIDE ARM FOR MEDICAL APPLICATIONS

This application is a continuation of U.S. patent application Ser. No. 08/804,913, filed on Feb. 25, 1997, which in turn claims the benefit under 35 U.S. C. §19(e) of U.S. Provisional Application Ser. No. 60/012,302, filed on Feb. 26, 1996.

BACKGROUND OF THE INVENTION

A need exists in the medical field for a positioning arm for holding and stabilizing devices used in medical procedures. For example, in the field of breast biopsy, a biopsy power driver and probe, such as that disclosed in U.S. Pat. No. 5,526,822, commonly assigned with the present application, is known for percutaneously obtaining tissue samples for analysis. However, to successfully perform the procedure, it is necessary to stabilize and restrain the power driver and probe to ensure accurate placement of the probe into the breast from any desired entry point. Furthermore, once the probe has been properly positioned within the patient at the lesion site, its position must be closely maintained for an extended period of time during the tissue sampling process. Presently, either the physician or an assistant to the physician performing the procedure often undertakes this function, but fatigue often results, leading to unintended movement of the probe. As a result, numerous attempts to accurately position the probe are often necessary. In a worst case, if the unintended movements due to human error are not detected by the practitioner, the location biopsied may not be the one desired.

SUMMARY OF THE INVENTION

The present invention solves the aforementioned problems by providing a device having great positional flexibility, which stabilizes and positions the biopsy power driver and probe as desired to ensure the ability to accurately place the probe into the breast and maintain position relative to the target tissue from any desired entry point.

More particularly, an apparatus is provided for securing and positioning medical instruments, which comprises a main arm having a generally vertical portion and a generally horizontal portion. A clamping assembly permits attachment of the apparatus to a stationary object, which is preferably an examination table. The clamping assembly comprises a locking clamp having a gripping mode and a releasing mode for alternately gripping and releasing the main arm, and a lever assembly for actuating the locking clamp between the gripping mode and the releasing mode. A horizontal clamp is attached to the generally horizontal portion of the main arm. An articulating arm assembly having a first arm portion, or upper arm, and a second arm portion, or forearm, is provided, wherein the upper arm and forearm are attached together by an elbow joint, so that they may be rotated relative to one another about a common axis. A proximal end of the upper arm is attached to the horizontal clamp by means of a shoulder joint, which preferably provides a rotational capability through a 360 degree range. Yet another joint, hereinafter referred to as a "wrist", is disposed at a distal end of the forearm, to which is attached a mounting bracket for securing a medical instrument, such as a biopsy power driver and probe, thereto. Both the elbow and wrist joints provide relative angular motion for the articulating arm portions. The articulating arm assembly is further adapted to swing out of the way while the patient is being positioned for a medical procedure.

One advantageous feature of the present invention is that the generally vertical main arm portion is adjustable in height, in order to compensate for anatomical variations in individual patients, and is adjustable radially in order to provide access to either side of the patient's body.

Another advantageous feature of the present invention is that the locking clamp is spring biased to its gripping position, so that it is only maintained in its releasing position by actuating (pushing or pulling) and holding the lever assembly, thereby ensuring that the main arm is held in a fixed position at all times other than when it is desired to adjust the relative position of the apparatus with respect to the patient. The lever assembly is particularly designed to ensure that it may be easily reached and actuated by a user standing anywhere along the head end or along either side of the examination table. This design preferably includes a laterally extending looped member which extends beneath the examination table such that portions of the looped member are proximate to each of the head end and two sides thereof. However, other configurations may be utilized as well, as long as they are of a symmetrical construction in order to provide ready access from any of the head end or either side of the table.

Still another advantageous feature of the invention is that the elbow joint attaching the upper arm and forearm of the articulating arm assembly comprises a spring loaded counterbalance mechanism which functions to support the weight of a medical instrument attached to the mounting bracket of the apparatus, thereby giving the instrument a weightless feel during the positioning process, which prevents fatigue on the part of a user and therefore permits more delicate and precise movements of the instrument.

Yet another advantageous feature of the invention is the inclusion of a micro-advance mechanism disposed distally of the aforementioned wrist joint, which, after fully restraining all clamps, permits fine adjustment of the linear position of a medical instrument attached to the mounting bracket. Significantly, the micro-advance mechanism is self-locking; i.e. it has sufficient friction such that it only moves upon actuation of an adjustment knob.

In another aspect of the invention, an apparatus for securing and guiding medical instruments is provided which comprises a main arm to which a medical instrument may be secured and a clamping assembly for attaching the main arm to an examination table. The examination table has a head end, a foot end, and two sides, and the clamping assembly comprises a locking clamp having a gripping mode and a releasing mode for alternately gripping and releasing the main arm, as well as a lever assembly for actuating the locking clamp between the gripping mode and the releasing mode. Advantageously, the lever assembly comprises a vertical member joined to the locking clamp and extending downwardly therefrom, and a laterally extending symmetrical member, which is preferably of a looped configuration, joined to the downwardly extending member. The looped member extends beneath the examination table such that portions of the looped member are proximate to each of the head end and the two side ends. It is conveniently located sufficiently inwardly from the table edges to prevent inadvertent actuation or release. With such a construction, a user may reach a portion of the looped member while standing at any of the head end or either side of the examination table and actuation of any portion of the looped member causes the vertical member to either swivel or move vertically, thereby actuating the locking clamp to the releasing mode.

In still another aspect of the invention, an apparatus for securing and guiding medical instruments is provided which comprises a main arm and an articulating arm assembly having a first end and a second end. The first end is attached to the main arm and the second end is attached to a holder to which a medical instrument may be mounted. Advantageously, a micro-advance mechanism is disposed at the second end for permitting fine adjustment of the linear position of a medical instrument attached to the holder.

The invention, together with additional features and advantages thereof, may best be understood by reference to the following description taken in conjunction with the accompanying illustrative drawing.

BRIEF DESCRIPTION OF THE DRAWINGS

FIG. 4 is a side view of the articulating guide arm shown in FIG. 1, illustrating the constructional details of spring-actuated counterbalance mechanism;

FIG. 5 is a cross-sectional view of the spring-actuated counterbalance mechanism illustrated in FIG. 4;

DETAILED DESCRIPTION OF THE DRAWINGS

Figure 1:
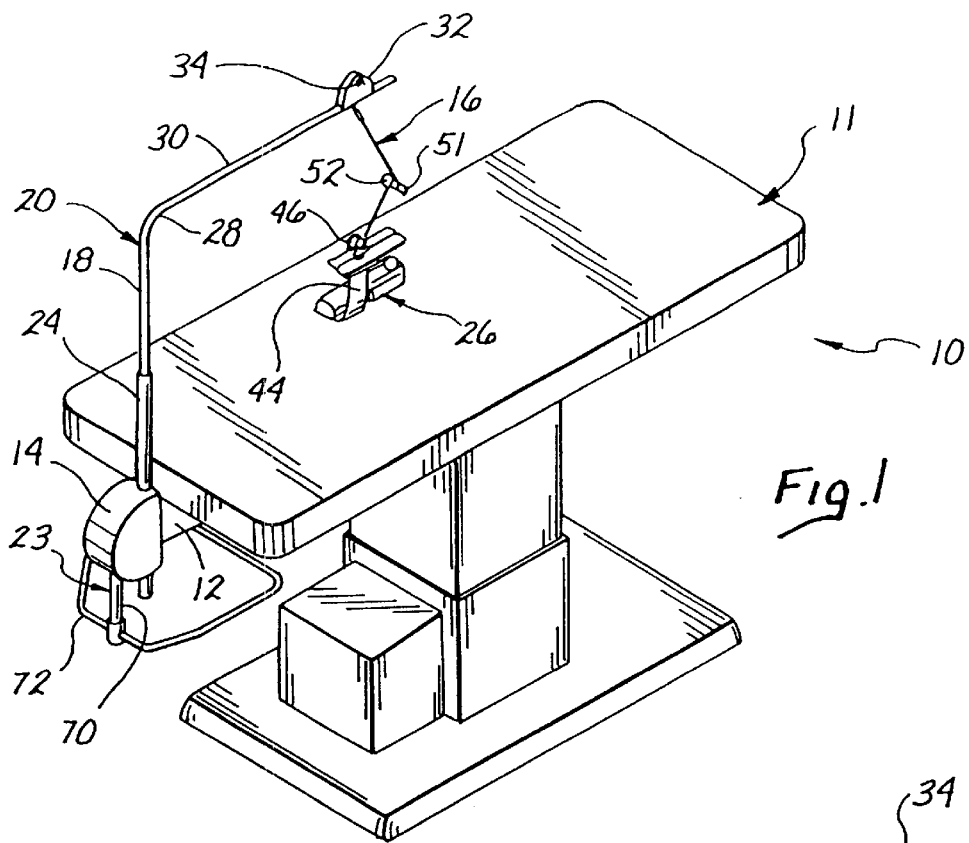
FIG. 1 is a perspective view showing an examination table which includes an articulating guide arm constructed in accordance with the principles of the invention.

Referring now more particularly to the drawings, there is shown in FIG. 1 an apparatus 10 comprising an examination table 11 having a table mount 12 at the head end, for providing a rigid stable platform onto which a table clamp block 14 may be mounted. The table clamp block 14 is utilized to attach an articulating arm assembly 16 to the table 11. A table mount for mounting the articulating arm assembly 16 is preferred, as opposed to a floor, wall, or ceiling mounted system, because it provides security in knowing that if the table were accidentally moved during a biopsy procedure, the biopsy probe would maintain its position relative to the patient. However, if desired, alternative mounting arrangements could be employed.

Figure 6:
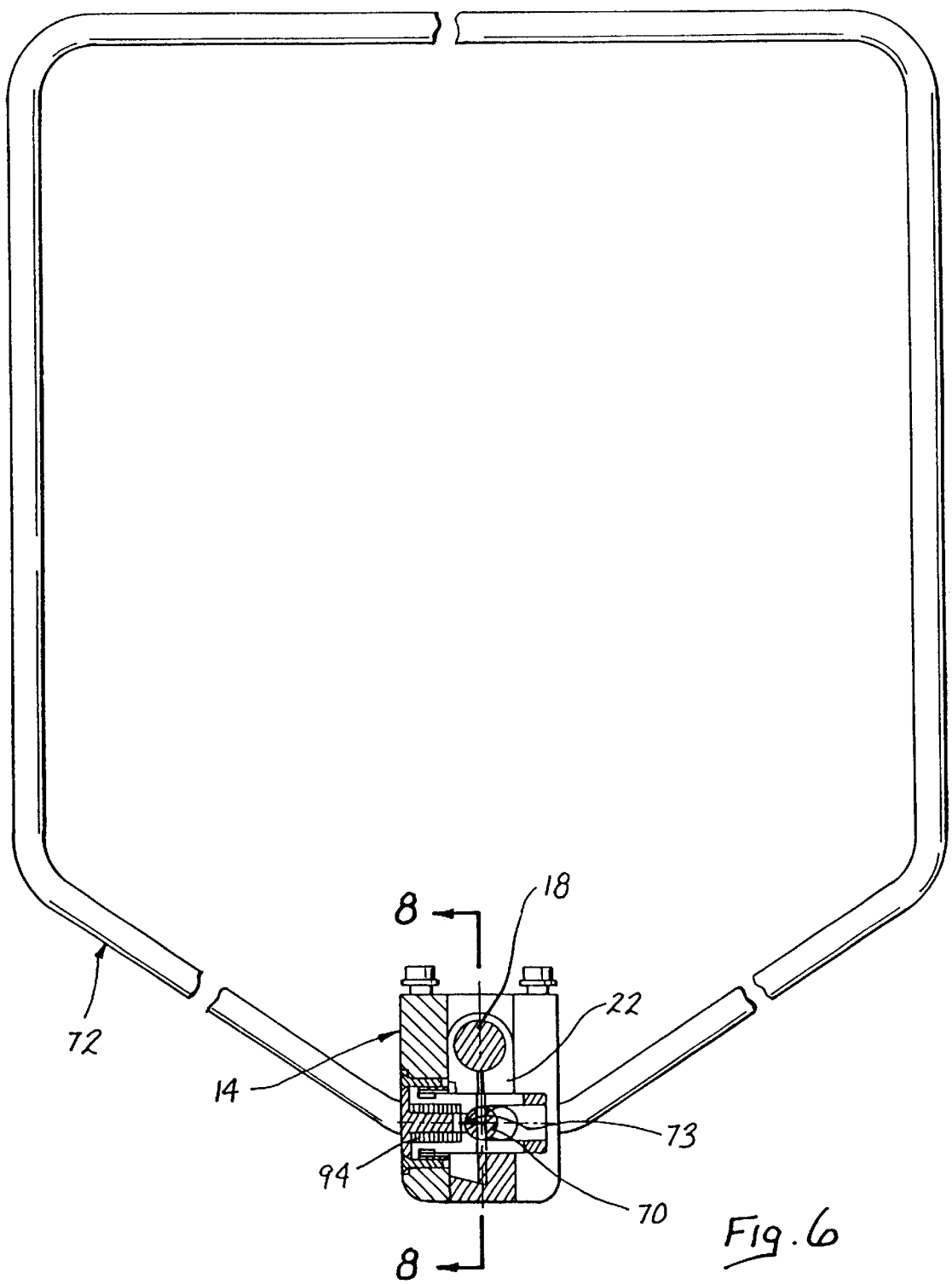
FIG. 6 is a top cross-sectional view, in isolation, of the clamping assembly for the articulating guide arm illustrated in FIG. 1.
Figure 8:
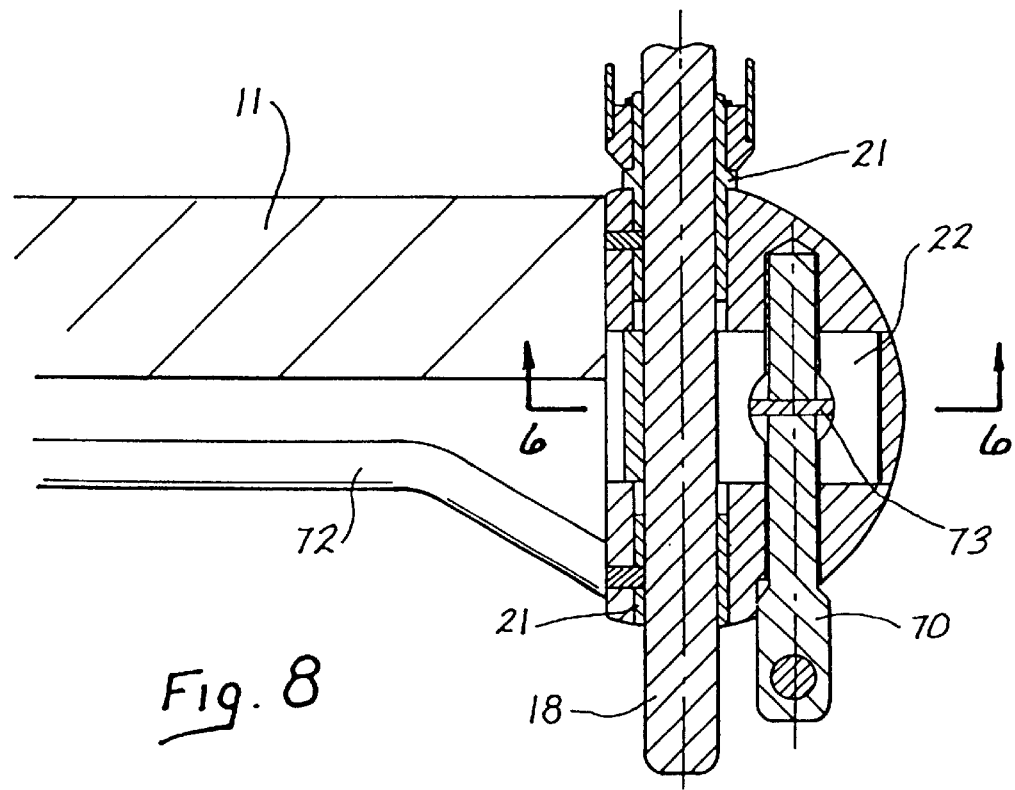
FIG. 8 is a side cross-sectional view of the clamping assembly of FIG. 1, illustrating the clamping assembly attached to an examination table.
Figure 9:
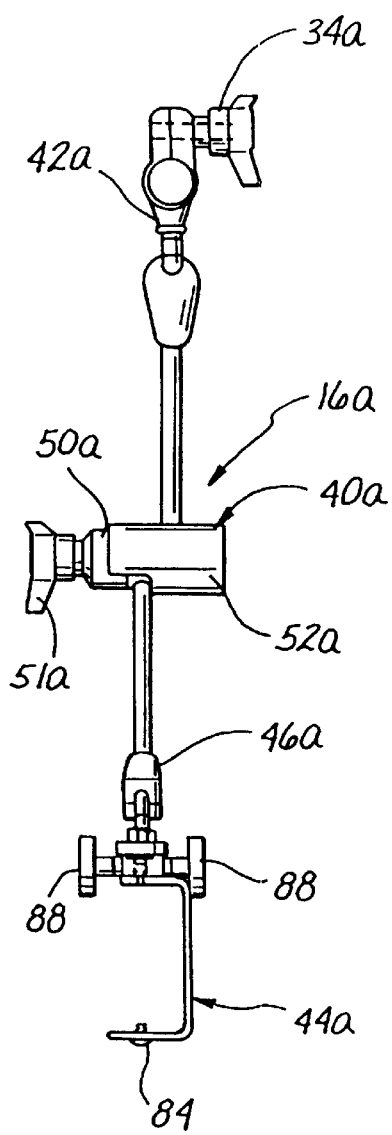
FIG. 9 is an end view, in isolation, of a modified embodiment of the articulating arm illustrated in FIG. 1.

A vertical leg 18 of a main arm 20 extends upwardly from the table clamp block 14, and is mounted thereto so that it may be held in any desired radial or vertical position. The table clamp block 14 comprises two bearings 21 (FIG. 8) which accept the leg 18, and a spring biased locking clamp 22 (FIG. 6) which is actuated by a lever assembly 23. The constructional details and particular advantages of the inventive clamp block 14 will be further described hereinbelow. The leg 18 may be rotated into any desired position by pushing the lever assembly 23, applying a lateral force, and maintaining application of that force while rotating the leg 18 (FIGS. 6 and 8). As soon as the lever assembly is released, the clamp 22 re-clamps the leg 18. This same procedure may be used to adjust the height of the arm 20, except that a height adjustment tube 24 is rotated instead of the main arm 20, while lateral force is applied to the lever assembly 23. The height adjustment tube 24 comprises a threaded bushing which engages an external thread on the main arm 20. The threaded portion of the main arm 20 is approximately six inches longer than the threaded bushing, thereby providing approximately six inches of vertical travel. The bottom face of the adjustment tube abuts the top bearing of the table clamp block bearing, and contact between these features is maintained by gravity and because of an interlocking relationship of the vertical fit assembly. It is important to be able to adjust the height of a biopsy driver 26 in this manner in order to compensate for anatomical variations in individual patients, and to accommodate for lesions at different elevations within a patient.

Figure 2:
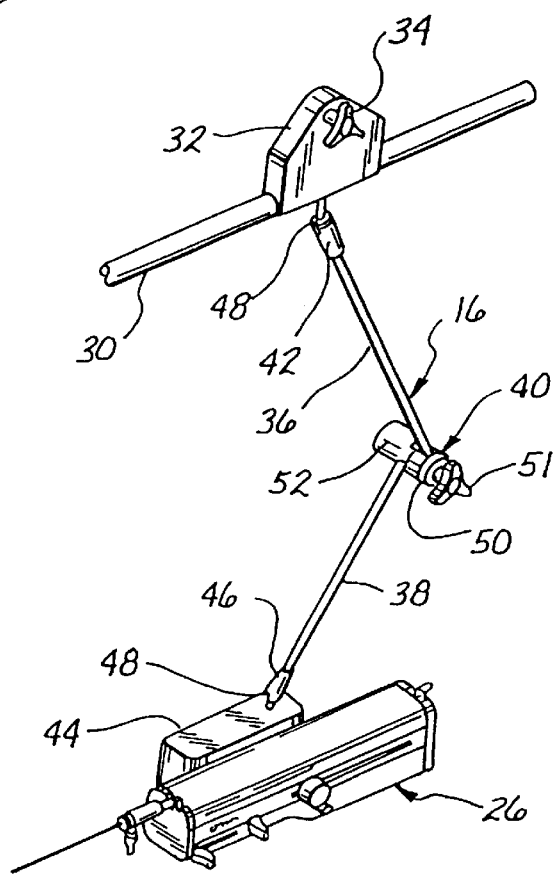
FIG. 2 is an enlarged perspective view, in isolation, of one embodiment of the articulating guide arm shown in FIG. 1.

The main arm 20 is preferably a structurally strong round bar having a 90 degree bend 28 disposed close to the midpoint of the bar. It is designed to be strong enough to support the weight of the biopsy driver 26 and articulating arm 16. Besides the vertical leg portion 18 and the bend 28, the arm 20 comprises a horizontal portion 30. On the horizontal arm portion 30 is disposed a horizontal clamp 32 which has a knob 34 for actuating the clamp between a clamped and an unclamped state (FIG. 2). Using the clamp 32, a physician may slide the articulating arm 16 and biopsy driver 26 along the horizontal arm portion 30, for proper positioning relative to a desired target tissue location within the patient.

Figure 3:
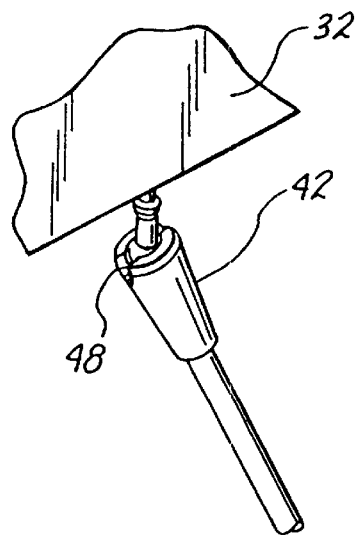
FIG. 3 is a detail top view of the ball joint forming a part of the inventive articulating guide arm.

Referring now more particularly to FIG. 2, the articulating arm 16 comprises an upper arm 36 and a lower arm or forearm 38. The two arm portions are joined by a rotating counterbalanced locking joint or elbow 40. The proximal end of the upper arm 36 is joined to the horizontal clamp 32 by means of an upper ball joint or shoulder 42, which is capable of rotation through a range of 360 degrees, and the distal end of the forearm 38 is joined to a mounting bracket 44 by means of a rotating joint or wrist 46. Ball joint 42 is shown in greater detail in FIG. 3. As illustrated, the shoulder joint 42 and rotating wrist 46 provide both radial and vertical adjustment through a 360 degree range, and include cut-outs 48 which maintain a particular desired orientation between the driver 26 and the articulating arm 16. A clamp 50 on the rotating elbow joint 40 actuates and simultaneously locks all three joints 40, 42, and 46, to provide a very wide range of vertical and radially positioned adjustments for the biopsy power driver 26. The clamp 50 is locked down and released by actuating a knob 51. An important feature of the invention is a spring actuated counterbalance mechanism 52, which is disposed at the elbow joint 40 and functions to support the weight of the biopsy driver 26, thereby creating a "weightless" feel which greatly improves tactile feel while advancing the biopsy probe into a lesion, and also reduces user fatigue.

Now with reference to FIGS. 4–5, the constructional details of the spring actuated counterbalance mechanism 52 are illustrated. The mechanism 52 includes a cylindrical cover 54 enclosing a retaining ring 56, a torsion spring 58, a sleeve 60, a center pin 62, and a bushing 64. Screws 66 and 68 function to fasten the bushing 64 to the rotating elbow joint and the cover 54 to the center pin 62, as illustrated best in FIG. 5.

The biopsy driver 26 is preferably a device for percutaneously obtaining tissue samples from lesions detected using radiological imaging techniques, as disclosed for example in U.S. Pat. No. 5,526,822 and U.S. patent application Ser. No. 08/386,941, now allowed, both of which are commonly assigned with the present application and herein expressly incorporated by reference. However, the apparatus is useful for any type of medical device, for example, which is otherwise hand held, and which requires fine manipulation during access and positioning, and further requires that such positioning be accurately maintained for an extended period of time (more than 60 seconds) relative to a patient. Examples of such medical devices include radio frequency and cryogenic probes, for example.

Figure 7:
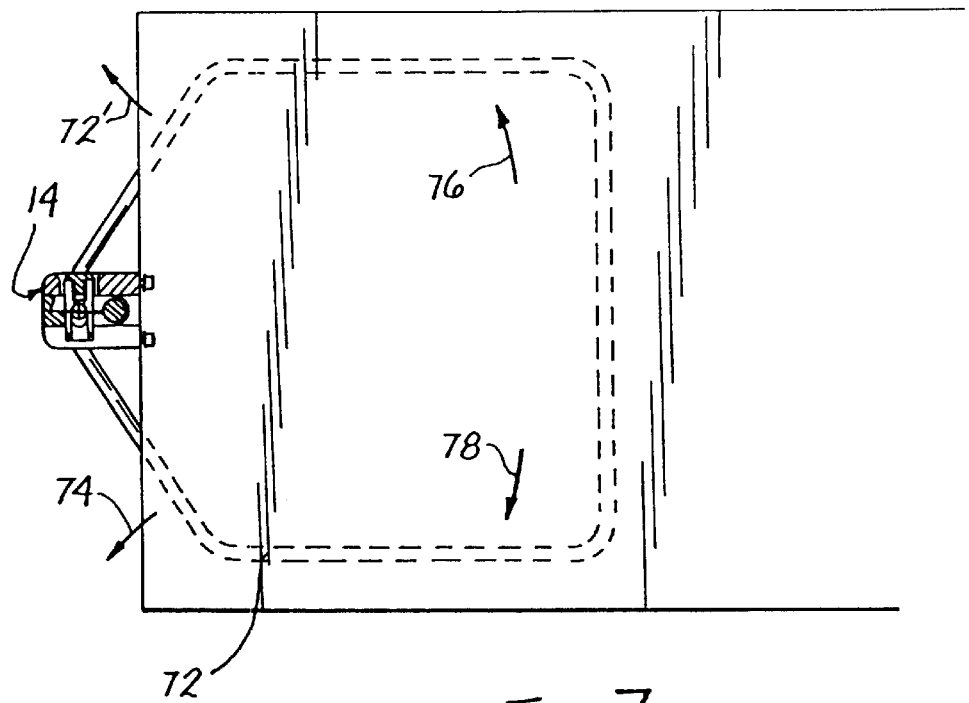
FIG. 7 is a cross-sectional view of the clamping assembly, similar to FIG. 6, illustrating the clamping assembly attached to the underside of an examination table.

A particularly advantageous feature of the invention is the constructional design of the table clamp block assembly 14, and, more particularly, that of the lever assembly 23. As illustrated especially in FIGS. 1, 6, and 7, the lever assembly 23 comprises a downwardly extending portion 70 which is joined to a tubular looped portion 72 extending beneath the table 11 so that it can readily reached and pulled by a person standing either at the head or on either side of the table 11. Actuation of the lever assembly 23 rotates a pin 73 (FIGS. 6 and 8) to compress disk springs 94 and thereby release the clamp 22. Thus, an individual preparing the apparatus 10 for use in a procedure is able to actuate the clamp 22, and thereby adjust the position of the horizontal and vertical portions of the main arm 30, by pulling or pushing on the looped portion 72 from wherever he or she happens to be standing about the table 11, in the direction of any of the arrows 72', 74, 76, or 78, for example (FIG. 7).

Figure 12:
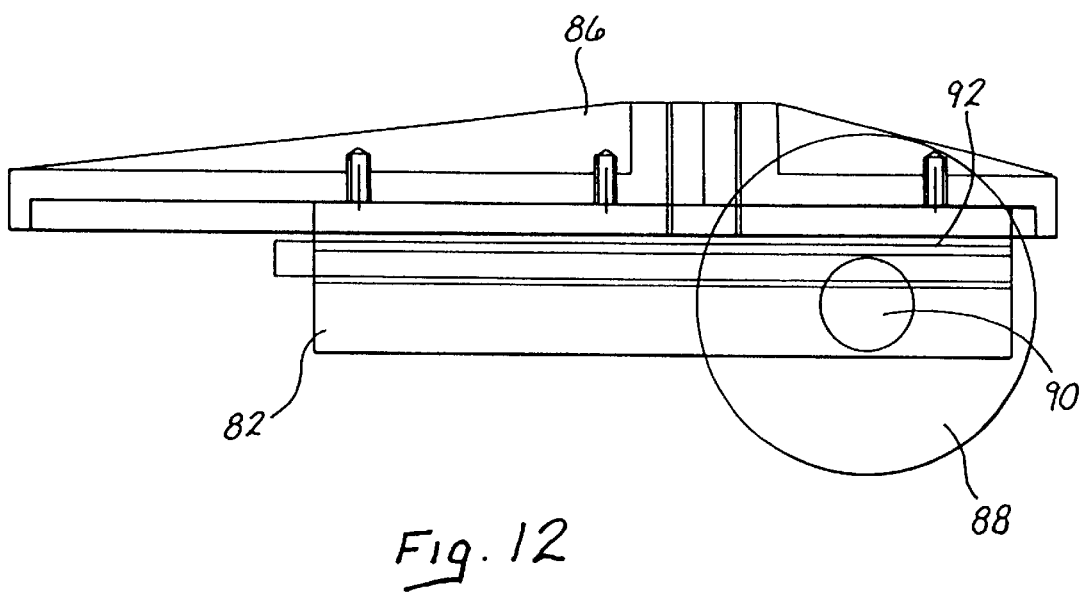
FIG. 12 is a schematic side view of the micro-advance mechanism illustrated in FIG. 11.

Another advantageous feature of the invention is illustrated in FIGS. 9–12, which figures show a modified, presently preferred, embodiment of the articulating arm assembly 16, like elements of the modified embodiment being designated by the same reference numerals as those used in the first embodiment, followed by the letter "a". The primary difference between this modified embodiment, and the embodiment illustrated in FIG. 2 is the inclusion of a micro-advance mechanism 81 for the bracket 44a, so that the linear position of the probe 26 respective to the patient may be finely adjusted after actuating knob 51a to lock clamp 50a and joints 42a and 46a. More particularly, the bracket 44a includes a holder 82 for mounting the driver and probe 26 by means of a mechanical fastener 84, such as a screw. The bracket further includes a top plate 86, which is attached at its upper end to the joint 46a, and at its lower end to the micro-advance mechanism 81. The micro-advance mechanism is constructed so that rotation of a linear advancement knob 88, mounted on either side of the micro-advance mechanism 81 (FIG. 11), will rotate a pinion gear 90 (FIG. 12). The pinion gear 90 engages a rack 92, so that rotation of the pinion gear 90 in one direction causes the rack 92 to move linearly in a first direction, and rotation of the pinion gear 90 in the other direction causes the rack 92 to move linearly in a direction opposite to the first direction. Since the holder 82 is fixedly connected to the rack 92, linear movement of the rack allows for travel of the holder 82, carrying the driver and probe 26, through a linear range of motion indicated by the distance x illustrated in FIG. 11.

Figure 10:
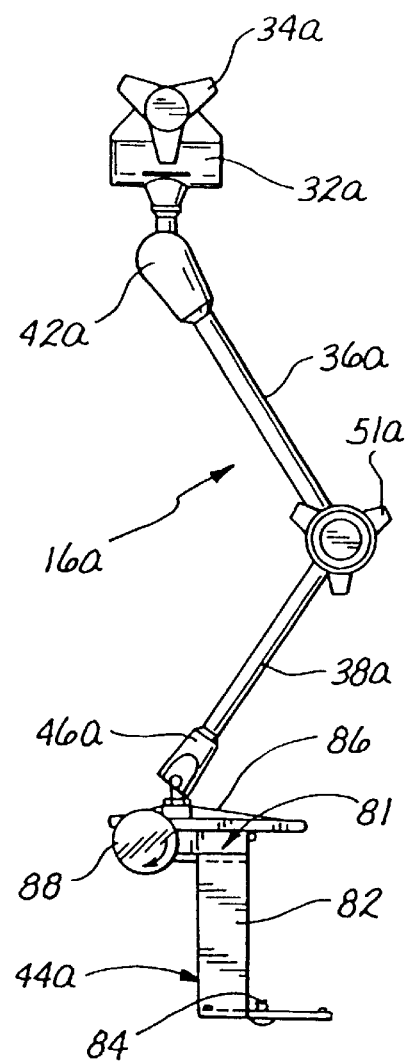
FIG. 10 is a side view, in isolation, of the articulating arm illustrated in FIG. 9.
Figure 11:
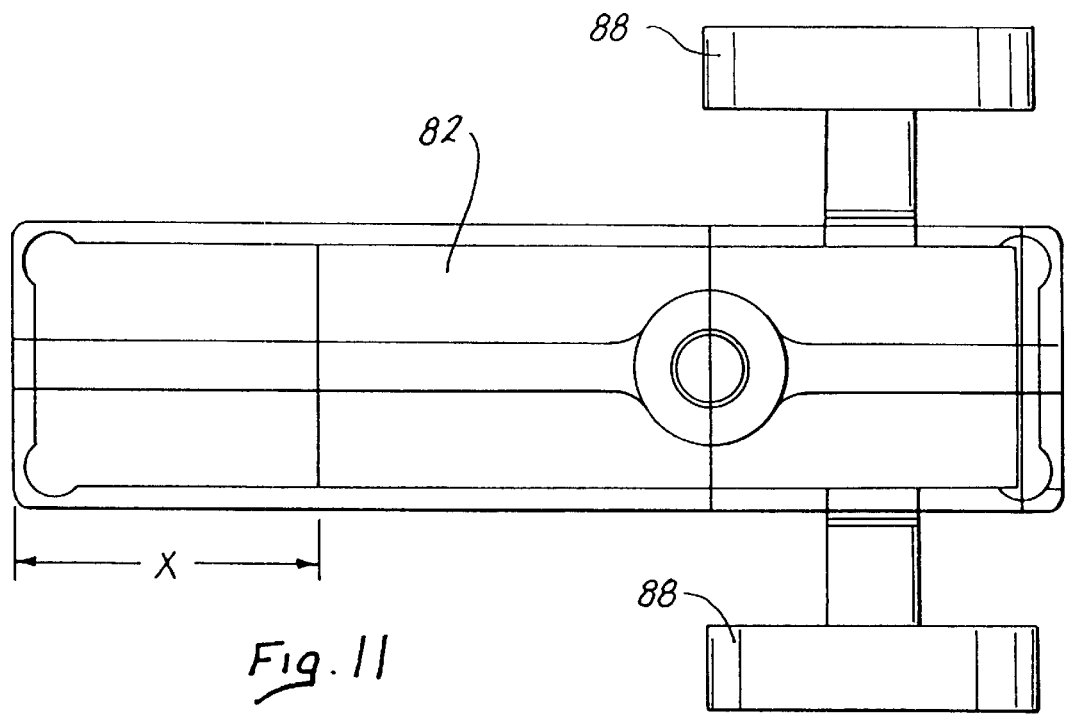
FIG. 11 is a schematic top view of a micro-advance mechanism constructed in accordance with the principles of the invention, for providing fine linear adjustment capability for a probe installed on the inventive articulating guide arm assembly.

In operation, the biopsy power driver and probe 26, or other suitable instrument, is installed securely to the bracket 44, 44a, using the fastener 84 (FIGS. 2 and 10). Then, the holder 82 is prepositioned to a point midway along the length of travel x (FIG. 11), by rotating the micro-advance stage knob 88. At this point in time, a patient may lie down on the examination table 11 in the supine position. The lever 23 is then actuated from any position on either side or at the head of the table 11 by pulling on the loop 72 to cause the spring actuated locking clamp 22 on the table clamp block 14 to open against the biasing force of springs 94 (FIG. 6), so that the main arm 20 may be rotated into a desired position to begin the biopsy procedure. The clamp 22 remains open as long as the lever 23 is being pulled. The height adjustment tube 24 may also be rotated to position the biopsy power driver 26 at an appropriate height for the particular patient on the table 11. Following this step, the clamp is reactivated to a locked position, merely by releasing the lever 23 and thereby allowing the springs 94 to bias the clamp to its closed and locked position.

At this point, the horizontal clamp 32 is unclamped, moved over the desired biopsy site on the patient's body, then re-clamped by turning knob 34 in a clockwise direction. Once the patient is prepared for the biopsy procedure, the clamp 50 is released, and the biopsy power driver and probe 26 is supported in one hand while the probe is advanced to the desired biopsy site. Once positioned, the knob 51 is turned to clamp and lock all three joints 40, 42, and 46, and both articulating arm portions 36 and 38, with a single fluid motion. At this point, if a fine axial adjustment of the position of the probe is necessary, this can be accomplished by rotating the knob 88 as desired. Then, the biopsy is taken, following which knob 88 is rotated to retract the probe out of the breast, or alternatively, the knob 51 is turned counterclockwise to unlock the clamp 50, and the probe is removed from the biopsy site. The clamp 22 in the table clamp block 14 is then released, by pulling on the loop 72 as described above, and the main arm 20, carrying power driver and probe 26, may then be swung away from its position over the table 11.

While this invention has been described with respect to various specific examples and embodiments, it is to be understood that the invention is not limited thereto and that it can be variously practiced within the scope of the following claims.

What is claimed is:

1. An apparatus for securing and positioning medical instruments, comprising:
   a main arm;
   an articulating arm assembly having a first end and a second end, the first end being attached to said main arm and the second end being attached to a holder to which a medical instrument may be mounted; and
   a micro-advance mechanism disposed at said second end for permitting fine adjustment of the linear position, relative to said second end, of a medical instrument attached to said holder;
   said micro-advance mechanism comprising an actuator which, when moved through a particular range of motion in a first direction, functions to actuate said holder to advance linearly a particular distance proportional to the range of motion through which the actuator is moved, and when moved through a particular range of motion in a second direction, functions to actuate said holder to retract linearly a particular distance proportional to the range of motion through which the actuator is moved.

2. The apparatus for securing and positioning medical instruments as recited in claim 1, wherein said actuator comprises a rotatable knob.

3. An apparatus for positioning a biopsy probe, the apparatus comprising:

a holder for supporting a biopsy probe;

an articulating arm assembly having a first end and a second end, the first end being associated with an apparatus support and the second end being associated with the holder adapted for supporting a biopsy probe; and a micro-advance mechanism comprising a gear for permitting fine adjustment of the linear position, relative to the second end of the articulating arm assembly, of a biopsy probe supported by the holder.

4. The apparatus of claim 3 wherein the micro-advance mechanism comprises an actuator associated with the gear.

5. The apparatus of claim 4 wherein the actuator comprises a rotatable knob having a diameter greater than the diameter of the gear.

6. The apparatus of claim 3 further comprising a biopsy driver supported by the holder.

7. An apparatus for positioning a biopsy probe, the apparatus comprising:

a holder for supporting a biopsy probe;

an articulating arm assembly having a first end and a second end, the first end being associated with an apparatus support and the second end being associated with the holder for supporting a biopsy probe;

a rack attached to the holder; and a pinion engaging the rack, wherein rotation of the pinion provides linear translation of a biopsy probe supported by the holder.

8. The apparatus of claim 7 further comprising an actuator associated with the pinion.

9. The apparatus of claim 8 wherein the actuator comprises a rotatable knob having a diameter greater than the diameter of the pinion.

10. The apparatus of claim 7 wherein the articulating arm assembly comprises a counterbalance mechanism.

* * * * *